United States Patent
Goerne et al.

(10) Patent No.: US 8,309,115 B2
(45) Date of Patent: Nov. 13, 2012

(54) MATRIX, CELL IMPLANTATION AND METHOD FOR THEIR PRODUCTION AND USE

(75) Inventors: Martin Goerne, Hamburg (DE); Peter Matthias Kaufmann, Wedemark (DE)

(73) Assignee: Humanautocell GmbH, Munich (DE)

( * ) Notice: Subject to any disclaimer, the term of this patent is extended or adjusted under 35 U.S.C. 154(b) by 242 days.

(21) Appl. No.: 12/578,624

(22) Filed: Oct. 14, 2009

(65) Prior Publication Data

US 2010/0028405 A1 Feb. 4, 2010

Related U.S. Application Data

(62) Division of application No. 10/559,331, filed as application No. PCT/EP2004/006140 on Jun. 7, 2004, now Pat. No. 7,618,646.

(30) Foreign Application Priority Data

Jun. 6, 2003 (DE) .................................. 103 25 807

(51) Int. Cl.
*A61F 2/02* (2006.01)
*C12N 11/02* (2006.01)
*C12N 11/10* (2006.01)
*C12N 11/08* (2006.01)

(52) U.S. Cl. ........ 424/425; 424/426; 435/177; 435/178; 435/180

(58) Field of Classification Search .................. 424/425, 424/426; 435/177, 178, 180
See application file for complete search history.

(56) References Cited

U.S. PATENT DOCUMENTS

| | | | |
|---|---|---|---|
| 5,626,861 A | 5/1997 | Laurencin et al. | |
| 6,103,255 A | 8/2000 | Levene et al. | |
| 6,337,198 B1 | 1/2002 | Levene et al. | |
| 6,605,039 B2 * | 8/2003 | Houben et al. | 600/365 |
| 2002/0045672 A1 | 4/2002 | Harris et al. | |
| 2002/0094514 A1 | 7/2002 | Bowlin et al. | |
| 2004/0063206 A1 | 4/2004 | Rowley et al. | |

FOREIGN PATENT DOCUMENTS

| | | |
|---|---|---|
| WO | 98/44027 | 10/1998 |
| WO | 99/09149 | 2/1999 |
| WO | 99/32204 | 7/1999 |
| WO | 01/35932 | 5/2001 |
| WO | 01/87575 | 11/2001 |
| WO | 03/064509 | 8/2003 |

OTHER PUBLICATIONS

Kneser et al., "Interaction of Hepatocytes and Pancreatic Islets Contransplanted in Polymeric Matrices," Virchows Archiv 435: 125-132 (1999).
Young, Picture Tests in Histology, Elsevier Health Sciences, Philadelphia, PA, (2001), p. 131.
Hanson, "Islet Viability Assessment by Single Cell Flow Cytometry," Dept. of Surgery, University of Wisconsin, Madison, online protocols, http://www.surgery.wisc.edu/transplant/research/fernandez/protocols/islet%20Viability%20Assessment%20by%20Single%20Cell%20Flow%20Cytometry.pdf., printed on Feb. 23, 2009.

* cited by examiner

*Primary Examiner* — Rosanne Kosson
(74) *Attorney, Agent, or Firm* — Oblon, Spivak, McClelland, Maier & Neustadt, L.L.P.

(57) ABSTRACT

The invention relates to porous matrices based on a biologically compatible polymer or polymer mixture, to a cell implantation that is established on said matrices and to additional cell implantation based on cell mixtures of hepatocytes and islets of Langerhans. The invention also relates to a method for producing porous matrices, to matrices obtained according to said method and to a special method for obtaining cells for the inoculation of an implantable matrix.

18 Claims, No Drawings

MATRIX, CELL IMPLANTATION AND METHOD FOR THEIR PRODUCTION AND USE

REFERENCE TO PRIOR APPLICATIONS

This application is a Divisional application of U.S. application Ser. No. 10/559,331, filed Nov. 16, 2006, now U.S. Pat. No. 7,618,646; which is a 371 application of PCT/EP/04/06140, filed Jun. 7, 2004; and claims priority to German patent application 103 25 807.8, filed Jun. 6, 2003, incorporated herein by reference.

BACKGROUND OF THE INVENTION

1. Field of the Invention

The present invention relates to porous matrices which are based on a biologically tolerated polymer or polymer mixture, to cell implants which build on the latter, to other cell implants which are based on cell mixtures composed of hepatozytes and islet of Langerhans cells, to a method for preparing porous matrices and to the matrices which can be obtained using this method, and to a special method for obtaining cells for inoculating an implantable matrix.

2. Description of Related Art

Tissue engineering is an interdisciplinary field which combines engineering and material sciences with medicine. The aim is to restore damaged tissue or improve its function.

The principle of tissue engineering is extremely simple: some cells are first of all removed from the patient and propagated in vitro. The propagated cells can then be embedded in a framework substance, resulting in the formation of a complete, live tissue replacement which is transplanted once again into the patient. In contrast to a conventional allogenic transplantation, which presupposes a suitable donor and as a rule requires life-long medicinal immuno-suppression, this method offers the crucial advantage of being able to use endogenous (autologous) cells.

The nature and construction of the framework substance employed, which is also termed matrix in that which follows, is of particular importance for the implants being accepted and being able to function. Apart from the material to be used, which is namely as a rule biologically degradable polymers, pore size, porosity and surface, just like pore shape, the morphology of the pore wall, and the connectivity between the pores, play a crucial role for the further development of the cells which are embedded in the framework substance and ultimately for the three dimensional construction of the tissue or organ to be regenerated.

Methods for producing biomatrices of this nature have already been disclosed. Thus, techniques from the textile field have already been applied for producing woven and nonwoven fibrous biomatrices. Another common method, in which salt crystals are first of all worked in to the biologically degradable polymer and then dissolved out again, makes it possible to control the pore size by way of the size of the salt particles and to control the porosity by way of the salt/polymer ratio (WO 98/44027). In a modification of the method, the biologically degradable polymers, which are dissolved in a solvent, are applied to what is termed a porogenic material, which is then once again dissolved out of the composite material, resulting in pores having the shape of the negative image of said porogenic material being left behind (WO 01/87575 A2). Coated matrices have also already been disclosed (see, for example, WO 99/09149 A1).

Nevertheless, the biomatrices which have thus far been produced using this method are not satisfactory in every case, in particular with regard to the acceptance and functional capacity of the implants which build on these matrices. In particular, no acceptable organ replacements have thus far been achieved using liver and pancreas implants.

BRIEF SUMMARY OF THE INVENTION

The invention achieves the object underlying the present invention, namely that of providing such a functional implant, by means of particular biomatrices and corresponding implants, which can be obtained using a special method.

The present invention therefore relates to the subject matter which is defined in the patent claims.

DETAILED DESCRIPTION OF THE INVENTION

The degree of porosity is the numerical specification in % of the fraction of the total volume of the matrix which is represented by the pore volume.

The word "pores" is used to designate the cavities which are present in the matrix according to the invention and which, in the present case, have an angular, in particular octagonal, shape in a 2-dimensional section and/or a canted shape when seen 3-dimensionally. The shape is furthermore preferably characterized by extensions such that the shape of the cavities can be compared with the shape of nerve cells. The size of a pore can be specified by means of a diameter, that is the mean of the longest and shortest diameters of the pores which can be discerned in a 2-dimensional section.

The matrix according to the invention possesses pores of different sizes, with the sizes being distributed (pore size distribution) over a particular range. According to the invention, it is of importance for a matrix to possess a wide pore size distribution. This distribution should extend from pores having a size in the range of about 150 µm to pores having a size in the range of about 300 µm, or be wider than this. Accordingly, a matrix according to the invention should, according to one aspect possess pores having a size of 150 µm or less. Matrices which possess pores having a size of 140 µm or less are preferred. Matrices which possess pores having a size of 130 µm or less are particularly advantageous. According to another aspect, a matrix according to the invention should possess pores having a size of 300 µm or more. Matrices which possess pores having a size of 350 µm or more are preferred. Matrices which possess pores having a size of 370 µm or more are particularly advantageous. The invention includes matrices which possess both pores having a size of 150, 140 or 130 µm, or less, and pores having a size of 300, 350 or 370 µm, or more. These values can be combined in any arbitrary manner to give minimum ranges over which the pore size distribution is to extend, with the ranges 150 to 300, 140 to 350 and 130 to 370 µm having to be mentioned, in particular. Particular preference is given to the given pore size distribution possessing frequency maxima outside the range of 150 to 300 µm, i.e. to a frequency maximum being above a pore size of 300 µm and to another frequency maximum being below a pore size of 150 µm.

A typical matrix according to the invention possesses the following pore size distribution. About 0.5% to 6%, preferably about 1% to 5%, even more preferably about 2% to 4% and, in particular, about 3%, pores having a mean diameter in the range of from 70 to 100 µm; about 2% to 8%, preferably about 3% to 7%, even more preferably about 4% to 6%, and, in particular, about 5%, pores having a mean diameter in the range of from 101 to 115 µm; about 2% to 8%, preferably about 3% to 7%, even more preferably about 4% to 6%, and, in particular, about 5%, pores having a mean diameter in the range of from 116 to 130 µm; about 1% to 7%, preferably about 2% to 6%, even more preferably about 3% to 5%, and, in particular, about 4%, pores having a mean diameter in the range of from 131 to 300 µm; about 11% to 23%, preferably about 13% to 21%, even more preferably about 15% to 19%, and, in particular, about 17%, pores having a mean diameter in the range of from 301 to 330 µm; about 4% to 10%, preferably about 5% to 9%, even more preferably about 6% to 8%, and, in particular, about 7%, pores having a mean diameter in the range of from 331 to 360 µm; about 5% to 17%, preferably about 7% to 15%, even more preferably about 9% to 13%, and, in particular, about 11%, pores having a mean diameter in the range of from 361 to 390 µm; about 7% to 19%, preferably about 9% to 17%, even more preferably about 11% to 15%, and, in particular, about 13%, pores having a mean diameter in the range of from 391 to 420 µm; about 3% to 9%, preferably about 4% to 8%, even more preferably about 5% to 7%, and, in particular, about 6%, pores having a mean diameter in the range of from 421 to 450 µm; about 12% to 24%, preferably about 14% to 22%, even more preferably about 16% to 20%, and, in particular, about 18%, pores having a mean diameter in the range of from 451 to 480 µm; and about 5% to 17%, preferably about 7% to 15%, even more preferably about 9% to 13%, and, in particular, about 11%, pores having a mean diameter in the range of from 481 to 510 µm. As a rule, therefore, a pore size distribution having more than one maximum is obtained, with this corresponding to a clustering of pores in more than one size range. This is of particular importance for the properties of matrices according to the invention.

The cavity volume, and thus the degree of porosity, are to be determined by porosimetry in a manner known per se.

The pore sizes, and thus the pore size distribution as well, can be determined, for example, by means of scanning electron microscopy. For this, thin sections of the matrix to be investigated are prepared and coated with gold. The scanning electron microscopic photographs are evaluated by measuring all the pores in a defined area, i.e. determining the longest and shortest diameters for each pore, determining the sum of the two values and dividing the sum by 2.

The term "matrix" refers to a three-dimensional support which is suitable for being colonized by cells. In this sense, the matrix serves as a three-dimensional template which can be colonized by cells or tissue. This colonization can take place in vitro or in vivo. Furthermore, the matrix serves, in connection with transplantations, for locating the transplant and also as a place holder for tissue which is gradually formed in vivo.

The polymer can in principle be any polymer which can be used in the field of medicine and, in particular, in transplantation medicine. Accordingly, polymers which are recognized by a host as being foreign but whose rejection can be suppressed by appropriate immunosuppression are also biologically tolerated. It is possible to use polymers which are essentially not biologically degradable. However, preference is given to polymers which are at least predominantly biologically degradable.

The expression "biologically degradable" refers to a material which living organisms (or body fluids or cell cultures which can derived from living organisms) are able to convert into metabolizable products. Biologically degradable polymers include, for example, polymers which are bioresorbable and/or bioerodible. "Bioerodible" denotes the ability to be soluble or suspendable in biological liquids. Bioresorbable means the ability to be able to be taken up by cells, tissues or fluids of a living organism.

In principle, biologically degradable polymers which are suitable in accordance with the invention include any polymers which can be used in the field of medicine, with this also including, for example, in addition to the polymers which are already established in the field of tissue engineering, polymers which have become established in active compound-releasing devices such as plasters and active compound implants.

Suitable natural polymers include, for example, polypeptides, such as albumin, fibrinogen, collagen and gelatin, and also polysaccharides, such as chitin, chitosan, alginate and agarose. These natural polymers can also be modified, where appropriate; for example, proteins such as collagen can be crosslinked.

Suitable synthetic polymers include, for example, particular polyanhydrides, in particular poly(sebacic acid-hexadecanoic diacid), poly(ε-caprolactone), poly(orthoesters) and, especially, poly(α-hydroxy-esters) such as poly(glycolic acid), poly(lactic acid) and poly(glycolic acid-lactic acid). Thus, the matrices and implants according to the invention are preferably based on biologically degradable polymers which contain the repeating units of the formula (I):

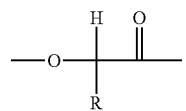

in which $R^1$ is hydrogen or methyl. With regard to the lactic acid units, the L form (the S enantiomer) is preferred. A particularly preferred polymer to be mentioned is poly(glycolic acid-lactic acid) having a glycolic acid to lactic acid ratio of from 99:1 to 1:99, preferably of from 10:90 to 90:10, for example 15:85, mol %.

Mixtures composed of two or more polymers can likewise be expedient.

In addition to the nature of the polymer, the molecular weight of the latter also determines the properties of the resulting matrix. It applies, in a general manner, that the porosity of the matrix decreases as the molecular weight of the polymer employed increases. This applies, in particular, when the material is foamed when preparing the matrix, i.e. is added under pressure together with a gas, such as $CO_2$, which initially dissolves in the polymer and forms pores when the pressure is lowered.

In addition, the crystallinity of the polymer employed affects the properties of the resulting matrix. In this case, it applies that the porosity of the resulting matrix generally increases as the crystallinity decreases, for which reason an amorphous polymer is preferred, in particular, for matrices which are of high porosity. This aspect is also of particular importance when the material is foamed during the preparation of the matrix.

The present invention furthermore relates to porous matrices which are based on a biologically degradable polymer and which are characterized in that the surface of the matrix is coated with at least one extracellular matrix protein.

Extracellular matrix proteins are well known. Those which are preferred according to the invention are collagens, in particular collagens of the I and IV type, laminin and fibronectin. These proteins can be prepared in purified form in a manner known per se or else obtained commercially. According to one embodiment, coatings of matrices according to the invention contain fibronectin as the extracellular matrix protein. According to another embodiment, coatings of matrices according to the invention contain a mixture of type I collagen, laminin and type IV collagen as the extracellular matrix protein, with preference being given, in this case, to the mixture containing the proteins in approximately equal percentages by weight.

According to the invention, particular preference is given to matrices which are coated in the above-described manner and which fulfill at least one of the following additional criteria:

the pores of the matrices exhibit the above-specified pore sizes or pore size distribution;
the degree of porosity is from 93 to 98%;
the pores exhibit the above-specified form;
the biologically degradable polymer is one of the above-specified natural or synthetic polymers, in particular poly(glycolic acid-lactic acid) having a lactic acid content of about 85 mol % and a glycolic acid content of about 15 mol %.

Matrices which are coated in this way can be obtained, for example, by immersing the uncoated matrix in a solution which contains the protein or protein mixture which is envisaged for the coating and then drying the matrix which has been wetted with the solution. In this connection, it is as a rule the case that, in dependence on the dimensions of the matrix body to be coated, the solution wets the outer regions of the matrix body, in particular, whereas comparatively little solution penetrates into the interior of the matrix body. This can result in the whole of the matrix surface not being coated uniformly but, instead, in the coating density decreasing from the outside inwards.

As an alternative, or in addition, to a coating, biologically active substances can be taken up in the polymer or even linked to it. These substances include, for example, synthetic active compounds (inorganic or organic molecules), proteins, polysaccharides and other sugars, lipids and nucleic acids which, for example, influence cell growth, cell migration, cell division, cell differentiation and/or tissue growth or possess therapeutic, prophylactic or diagnostic effects. Those which may be mentioned by way of example are vasoactive active compounds, neuroactive active compounds, hormones, growth factors, cytokines, steroids, anticoagulants, anti-inflammatory active compounds, immunomodulating active compounds, cytotoxic active compounds, antibiotics and antiviral active compounds.

The present invention also relates to a method for preparing a porous matrix which is based on a biologically tolerated polymer or polymer mixture and which is characterized in that a mixture composed of polymer particles and sodium chloride particles having a defined grain size is compacted and the sodium chloride is then dissolved out.

Polymer particles having a grain size in the range of from about 20 to 950 µm, advantageously in the range of from about 20 to 760 µm, and, in particular, in the range of from about 108 to 250 µm, and sodium chloride particles having a grain size in the range of from about 90 to 670 µm, advantageously in the range of from about 110 to 520 µm, and, in particular, in the range of from about 250 to 425 µm, have proved to be expedient for establishing the desired pore sizes or pore size distribution. Furthermore, a ratio by weight of polymer particles to sodium chloride particles in the range of from 1:100 to 1:10, advantageously in the range of from 1:50 to 1:15, and, in particular, in the range of from about 1:20 to 1:18, has proved to be expedient for establishing the desired porosity.

It has furthermore proved to be expedient to use salt and polymer having a specific grain size distribution. As far as the sodium chloride which is used for preparing the matrix is concerned, it is advantageous for the content of salt having a grain size of from 250 µm to 320 µm to be from about 15% to 50%, advantageously from about 18% to 42%, and preferably from about 22% to 28%; for the content of salt having a grain size of from 330 µm to 380 µm to be from about 20% to 65%, advantageously from about 30% to 52%, and preferably from about 42% to 46%; and for the content of salt having a grain size of from 390 µm to 425 µm to be from about 15% to 62%, advantageously from about 25% to 42%, and preferably from about 29% to 33%, with the percentage values referring to the total weight of salt used for the preparation. This does not thereby exclude fractions having grain sizes above and/or below the specified ranges.

According to a special embodiment, it has proved to be advantageous for the content of sodium chloride particles having a grain size of from 108 µm to 140 µm to be from 1 to 15% by weight, preferably from 4 to 12% by weight, and in particular from 7 to 9% by weight, for the content of salt having a grain size of from 145 µm to 180 µm to be from 1 to 11% by weight, preferably from 3 to 9% by weight, and in particular from 5 to 7% by weight, for the content of salt having a grain size of from 185 µm to 220 µm to be from 3 to 21% by weight, preferably from 7 to 17% by weight, and in particular from 10 to 14% by weight, for the content of salt having a grain size of from 225 µm to 250 µm to be from 1 to 11% by weight, preferably from 3 to 9% by weight, and in particular from 5 to 7% by weight, for the content of salt having a grain size of from 250 µm to 320 µm to be from 15 to 50% by weight, preferably from 18 to 42% by weight, and in particular from 22 to 28% by weight, for the content of salt having a grain size of from 330 µm to 380 µm to be from 15 to 50% by weight, preferably from 18 to 42% by weight, and in particular from 22 to 28% by weight, and for the content of salt having a grain size of from 390 µm to 425 µm to be from 5 to 29% by weight, preferably from 10 to 24% by weight, and in particular from 15 to 19% by weight.

As far as the polymer which is used for preparing the matrix is concerned, it is advantageous for the content of polymer having a grain size of from 108 µm to 140 µm to be from about 5% to 50%, advantageously from about 10% to 30%, and preferably from about 14% to 18%; for the content of polymer having a grain size of from 145 µm to 180 µm to be from about 10% to 55%, advantageously from about 15% to 40%, and preferably from about 20% to 24%; for the content of polymer having a grain size of from 185 µm to 220 µm to be from about 18% to 88%, advantageously from about 32% to 76%, and preferably from about 43% to 49%, and for the content of polymer having a grain size of from 225 µm to 250 µm to be from about 5% to 45%, advantageously from about 10% to 28%, and preferably from about 14% to 18%, with the percentage values referring to the total weight of polymer used for the preparation.

In order to obtain salt and/or polymer particles of the desired grain size distribution, it is as a rule expedient to first of all comminute the commercially available product. This can be effected in devices which are customary for this purpose, for example impact systems or grinding mills. However, that which is determining for the desired grain size distribution is the subsequent screening using customary analytical screens.

The compacting is preferably effected by the action of pressure. For this, the polymer/sodium chloride mixture can be pressed in a conventional hydraulic press at a ram pressure in the range of from about 780 psi to 1450 psi, advantageously in the range of from about 840 psi to about 1230 psi, and in particular in the range from about 900 psi to 1100 psi. It has proved to be expedient to allow the pressure to act for from about 10 s to 360 s, advantageously from about 40 s to 180 s, and in particular from about 50 s to 70 s, at temperatures in the range from 18° C. to 25° C.

The sodium chloride is dissolved out, for example, using water or aqueous solutions. First, the compacted mixture (matrix blank) can be soaked for from about 1 h to 80 h, advantageously from about 12 h to 62 h, and in particular from about 36 h to 60 h.

It is furthermore advantageous for the compacted mixture to be initially stored in a $CO_2$ atmosphere prior to the sodium chloride being dissolved out. Thus, for example, the compacted mixture can be gassed at a $CO_2$ pressure in the range of from about 140 psi to 1650 psi, advantageously in the range of from about 360 psi to 1120 psi, and, in particular, in the range of from about 800 psi to 900 psi, with times in the range of from about 1 h to 180 h, advantageously in the range of from about 3 h to 60 h, and, in particular, in the range of from about 12 h to 36 h, having proved to be expedient in this connection. After that, the pressure is reduced, with the rate at which the pressure is lowered having an influence on the pore formation. Although the use of $CO_2$ is preferred, other gases, such as air, nitrogen, helium, neon, krypton, argon, xenon or oxygen can likewise be suitable. Subsequently, the water or the aqueous solution is, with a view to drying, removed in a manner known per se. To achieve this, the matrix can, for example, be laid on absorbent paper.

According to a preferred embodiment, a polymer solution is added to the mixture composed of polymer particles and sodium chloride particles, and the solvent is removed, before compacting is effected. In this connection, the polymer particles and the polymer solution can be based on the same polymer. However, the polymers can also be different polymers, in particular polymers having different biological degradabilities. The of polymer solution has the advantage that what are in effect supporting pillars are erected in the matrix, with this making it possible to improve the mechanical properties of the matrix. In particular, a matrix of this nature exhibits less tendency to crumble.

The solvent which is used should dissolve the polymer but not the salt. This ensures that the porogenic properties of the salt are not, or are only insignificantly, affected. Acetone, ethyl acetate, methylene chloride, chloroform, hexafluoroisopropanol, chlorinated and fluorinated, aliphatic and aromatic hydrocarbons, tetrahydrofuran, ethyl methyl ketone, diethyl ketone, and mixtures thereof, are, for example, suitable for dissolving the abovementioned polymers. Chloroform is, in particular, suitable for dissolving poly(glycolic acid), poly(lactic acid) or poly(glycolic acid-lactic acid), and also suitable with a view to the medical use.

Admixing the polymer solution and the polymer particle/salt particle mixture initially results in a stirrable paste which then rapidly becomes solid as the solvent is removed. The concentration of the polymer in the solution is expediently to be chosen such that the polymer is completely dissolved, on the one hand, and, on the other hand, the solvent can be removed rapidly without the polymer particles beginning to dissolve to any significant extent.

A weight ratio of polymer particles to dissolved polymer of from 10:1 to 1:100, advantageously of from 2:1 to 1:25, and in particular of from 1:1 to 1:10, has proved to be beneficial.

As far as the weight ratio of polymer particles to sodium chloride particles is concerned, it is possible, within the context of this embodiment, to select a weight ratio which is higher with respect to sodium chloride, i.e. of up to 1:200, 1:500 or 1:1000, with the weight ratio of total polymer to sodium chloride still being greater than 1:100. In this way, it is possible to obtain porosities of greater than 98%.

In the above-described method, the sodium chloride serves as a porogenic material which, by definition, is understood as being a solid, or at least semisolid, material which initially unites with the matrix-forming polymer to give a mixture and which is then removed from the mixture, resulting in the formation of cavities (pores). For this, it is expedient for the porogenic material to be soluble in at least one solvent and to be essentially insoluble in at least one further solvent. A material is essentially insoluble when, in particular, it is less than 30% by weight, preferably less than 20% by weight, in particular less than 10% by weight, for example less than 5, 4, 3, 2 and 1% by weight, soluble under the processing conditions, i.e. as a rule at temperatures in the range from 18° C. to 25° C. and under atmospheric pressure.

The structure and properties of the resulting matrices are essentially determined by the porogenic material which is used for preparing them. In this connection, it is not only the nature of the porogenic material which is important but also, especially, the grain size distribution of the porogenic particles. Thus, it applies, in general, that not only the pore size but also the connectivity, i.e. the network of cavities which communicate with each other, increase as the grain size increases. This network, which is also termed macrostructure or macroporous structure, is to be distinguished from the pores which can be obtained by foaming and which are as a rule closed and therefore form a structure which is designated a microstructure or microporous structure.

Method for preparing a porous matrix based on a biologically tolerated polymer or polymer mixture, characterized in that a mixture composed of polymer particles, particles of a porogenic material and a polymer solution is compacted and the porogenic material is then dissolved out.

This method is in principle not restricted to the previously described features. Thus, the polymer can be selected from polyanhydrides, poly(orthoesters), poly(α-hydroxyesters), poly(ester amides), polyamides, poly(ester ethers), polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinyl pyrrolidones, polysiloxanes, polystyrenes, poly-urethanes, derivatized celluloses and (meth)acrylic acid polymers and copolymers. While the porogenic material is preferably selected from water-soluble salts, e.g. sodium chloride, potassium chloride, sodium fluoride, potassium fluoride, sodium iodide, potassium iodide, sodium nitrate, sodium sulfate, sodium citrate, sodium tartrate, sugars (e.g. sucrose, fructose and glucose) and mixtures thereof, the material can also be selected from waxy substances such as paraffins, beeswax and the like. In principle, polymer, porogenic material and the solvent used for forming the solution are to be matched to each other such that the solution contains polymer in dissolved form and polymer particles in solid form and the porogenic material essentially remains undissolved.

The matrices which can be obtained using the above-described methods are likewise part of the subject matter of the present invention.

The present invention also relates to implants which comprise at least one of the above-described matrices and at least one cell. In this connection, the cells can be selected, in particular, from liver cells, pancreas cells, fat cells, intestine cells, skin cells, blood vessel cells, nerve cells, muscle cells, thyroid gland cells and tooth root cells, according to the purpose of the implant. Special embodiments of implants according to the invention relate to liver cells and pancreas cells.

The present invention furthermore relates to implants which comprise at least one matrix based on a biologically tolerated polymer and cells of at least two cell types, with the cells of the first cell type being hepatocytes and the cells of the second cell type being islet of Langerhans cells. This subject matter is not restricted to the above-described matrices, i.e. implants based on the matrices according to the invention.

Particular ratios of hepatocytes to islet of Langerhans cells are advantageous according to the purpose of the implant, i.e. in particular the function to be fulfilled. Thus, one embodiment of the invention relates to implants which, after implantation, exhibit the endocrinal properties of an equivalent pancreas organ. A ratio of hepatocytes to islet of Langerhans cells of about $10^6$:3000 has proved to be advantageous for this purpose. Another embodiment of the invention relates to implants which, after implantation, carry out metabolic functions of a liver. A ratio of hepatocytes to islet of Langerhans cells of about $10^6$:3-200, advantageously of $10^6$:10-100, in particular of $10^6$:20-80 and, particularly preferably, of about $10^6$:35-45, has proved to be expedient for this purpose.

It may be noted that such implants as a rule contain other cells in addition to hepatocytes and islet of Langerhans cells, namely and, in particular, other liver cells and pancreas cells which accrue concomitantly in connection with the isolation of the cells.

The cells or cell mixtures which are to be used for colonizing matrices according to the invention can be obtained in a manner known per se. For the purpose of producing an autologous implant, the cells are preferably derived from the individual into whom the implant is to be inserted. Thus, suitable tissue, for example a portion of liver or pancreas, is as a rule removed from the individual and prepared in a suitable way for the inoculation and culturing the matrix in vitro. In this connection, it is of importance that the cells exhibit a vitality rate which is as high as possible.

If liver cells are being obtained from the liver tissue, account has to be taken of the fact that the liver cells are surrounded by a thick connective tissue layer, particularly in the case of a liver cirrhosis. According to the invention, solutions of defined composition are used in order to be able to isolate the liver cells containing a proportion of vital cells which is as high as possible.

The present invention therefore relates to an aqueous composition A which contains NaCl, KCl and HEPES and has a pH of about 7.4, and to its use for perfusing a portion of liver or pancreas. In particular, 1000 ml of this solution contain about 8.3 g of NaCl, 0.5 g of KCl and 2.38 g of HEPES. The perfusion is preferably carried out at a temperature of about 37° C. and a flow rate of about 30 ml/min. A few minutes, in particular from about 5 to 120 minutes, for example about 7 minutes, are sufficient for perfusing the tissue portion adequately at the abovementioned flow rate.

Alternatively, it is also possible to use an aqueous composition A' which contains ethylene glycol tetraacetic acid (EGTA) for perfusing a portion of liver or pancreas.

The present invention furthermore relates to an aqueous composition B which has a pH of from about 7.3 to 7.4, preferably about 7.35, and which contains NaCl, KCl, HEPES, $CaCl_2$, collagenase and trypsin inhibitor, as well as to its use for perfusing a portion of liver or pancreas. 1000 ml of the solution preferably contain 8.3 g of NaCl, 0.5 g of KCl, 2.38 g of HEPES, 0.7 g of $CaCl_2 \times 2H_2O$, 500 mg of collagenase H and 7.5 mg of trypsin inhibitor. In this case, too, perfusing at about 37° C. and a flow rate of about 30 ml/min has proved to be expedient. A few minutes, in particular from about 5 to 10 minutes, for example about 6 to 7 minutes, are sufficient for perfusing the tissue portion adequately.

Alternatively, it is also possible to use an aqueous composition B', which contains collagenase and hyaluronidase, for perfusing a portion of liver or pancreas. 1000 ml of the solution preferably contain from 5 to 10 U of collagenase/ml and from 5 to 10 U of hyaluronidase/ml.

It is advantageous for the vitality of the cells to be isolated if the tissue portion is initially treated with composition A and then treated with composition B. Alternatively, it is possible to use a composition A' initially and then to use a composition B'.

Following on from the perfusion, the tissue portion can then be dissected out and carefully shaken in a suitable medium, for example Williams medium E. If the resulting cell suspension still contains relatively coarse cell debris, the latter can be removed in a manner known per se, for example by filtering the cell suspension through a nylon net (200 µm). The cells of the filtrate can then be pelleted carefully, in connection with which a three-minute centrifugation at 50 g and 4° C. has proved to be advantageous.

The cells which have been isolated are loaded onto the matrices in a manner known per se. As a rule, the cells are loaded onto the matrix as a cell-containing solution and the cells and matrix are then incubated, usually under cell culture conditions, until cells adhere to the matrix. If more than one cell type for example hepatocytes and islet of Langerhans cells, is being loaded onto a matrix, the different cell types can in principle be loaded on jointly or else consecutively. According to a special embodiment, islet of Langerhans cells are loaded on initially, followed by hepatocytes, with an incubation in each case being carried out after the loading until at least a part of the cells is adhering to the matrix.

Matrices and implants according to the invention exhibit crucial advantages. Thus, the internal dimensions enable the matrices to be efficiently colonized with cells. The matrices are, on the one hand, freely moldable and, on the other hand, provide adequate stability and rigidity for withstanding the surgical implantation procedure and resisting the mechanical forces acting at the implantation site. The initial cell destruction, which sets in after the implantation, is limited, and, after a short time, implanted tissue can assume the intended function. Shortly after the implantation, blood vessels or blood vessel-rich granulation tissue, and also nervous tissue, begin to proliferate into the implant. The matrices according to the invention can be prepared without having to use physiologically harmful solvents, for example formaldehyde, which means that no special method is required for eliminating the solvents and there is no danger of residual quantities of these solvents remaining.

Matrices and implants according to the invention have many different possible uses. Those which may be mentioned, in particular, are uses in the medical field. The present invention therefore also relates to the matrices and implants according to the invention for therapeutic use.

A special use in this field is that of synthesizing tissue (tissue engineering). In this case, the matrices according to the invention serve more or less as scaffolds into which cells migrate and/or onto which cells adhere.

For this, the matrices can, for example, be inoculated with the desired cells in vitro, i.e. treated with a cell-containing solution and incubated until cells have adhered to the matrix. Such a matrix together with cells adhering to it (referred to here as an implant) can then be subjected to further procedural steps, for example further culturing, where appropriate under the influence of active compounds, e.g. for the purpose of further expanding the cells or modifying their properties, and/or be stored until implantation in a suitable manner, for example on ice or in a bioflow reactor under standard conditions. In the context of this use, it is advantageous to be able to initially isolate, and, where appropriate, also expand, in vitro the cells which are intended for the implantation. In particular, this thereby makes it possible to apply different cell types, such as the above-described hepatocytes together with islet of Langerhans cells, to a matrix.

Instead of an in vitro inoculation, another possibility is to implant the matrix (without any prior cell adhesion) with the aim of inducing precursor cells, which are capable of tissue regeneration, to migrate into a damaged tissue and there regenerate tissue which has been lost. For this, the matrix must be configured such that desired cells, but not undesired cells, can migrate into the matrix. Such a use is generally described as being guided tissue regeneration (GTR).

A matrix according to the invention or an implant according to the invention can therefore be used for treating the human or animal body. For this, one or more matrices, or one or more implants, is/are introduced into the body to be treated by way of a surgical intervention. If the implant contains cells having an organ function, or if cells having an organ function are to migrate into the matrix, as is the case, for example, with hepatocytes or islet of Langerhans cells, the matrices or implants can, for example, be implanted into the mesenterium, subcutaneous tissue, retroperitoneum, properitoneal space or intramuscular space of the individual to be treated.

In principle, any individuals who require an appropriate tissue replacement can be treated with the matrices or implants according to the invention. These individuals are as a rule individuals who are suffering from a specific disturbance or disease whose course involves the loss of functional tissue. This may potentially affect whole organs, for example the liver or the pancreas. Thus, the present invention is directed, in particular, towards treating diseases which lead to chronic liver or pancreas failure. These diseases include, for example, chronic hepatitis and biliary cirrhosis in adults as well as biliary atresia and congenital metabolic defects in children. A liver transplantation can also be indicated in the case of liver carcinomas. On the other hand, a pancreas transplantation is indicated, in particular, in the case of all forms of diabetes mellitus, in particular type I or type II diabetes mellitus.

The present invention therefore also relates to the use of a matrix according to the invention or of an implant according to the invention in making available a therapeutic agent for carrying out a transplantation on an individual and, in this connection, in particular for treating an individual who is suffering from an at least partial loss of functional tissue which is to be replaced by the transplant.

The following examples are intended to illustrate the invention without restricting its scope.

EXAMPLE 1

Preparing the Matrix a) Without Polymer Solution

Polymer pellets (Resomer® RG 853, obtainable from Boehringer, Ingelheim) are frozen in liquid nitrogen and shredded in the frozen state (Däschle impact system; 12000 rpm, 2 min). The shredded polymer particles are screened. Particles having a size of from 108 µm to 250 µm are used for preparing the matrix. In this connection, 16% by weight of the polymer employed has a particle size of between 108 µm and 140 µm, while 22% by weight of the polymer employed has a particle size of between 145 µm and 180 µm, 46% by weight of the polymer employed has a particle size of between 185 µm and 220 µm and 16% by weight of the polymer employed has a particle size of between 225 µm and 250 µm. Sodium chloride (common salt) is screened and sodium chloride particles having a grain size of from 250 µm to 425 µm are used for preparing the matrix. In this connection, 25% by weight of the salt employed has a particle size of between 250 µm and 320 µm, 44% by weight of the salt employed has a particle size of between 330 µm and 380 µm and 31% by weight of the salt employed has a particle size of between 390 µm and 425 µm. 760 mg of sodium chloride particles and 40 mg of polymer particles are mixed with each other. The mixture is introduced into a punching die and pressed with a hydraulic press for 1 minute at a ram pressure of 1000 psi. After that, the matrix blanks are laid on a Teflon plate and gassed for 24 hours in a $CO$ atmosphere (850 psi). The blanks are then soaked for 24 hours in order to dissolve out the enclosed salt grains. Finally, the matrices are dried for 12 hours on absorbent paper.

The resulting polymer matrix has a porosity of 95±2% and a defined pore size, which is determined by means of scanning electron microscopy, of 250 µm±120 µm.

b) With Polymer Solution

Sodium chloride (analytically pure) is ground (Däschler impact system; 12000 rpm, 2 min) and then screened and sodium chloride particles having a grain size of 108 to 425 µm are used for preparing the matrix. In this connection, 8% of the salt employed has a particle size of between 108 µm and 140 µm, while 6% by weight of the salt employed has a particle size of between 145 µm and 180 µm, 12% by weight of the salt employed has a particle size of between 185 µm and 220 µm, 6% by weight of the salt employed has a particle size of between 225 µm and 250 µm, 25% by weight of the salt employed has a particle size of between 250 µm and 320 µm, 26% by weight of the salt employed has a particle size of between 330 µm and 380 µm and 17% by weight of the salt employed has a particle size of between 390 µm and 425 µm. 96 g of sodium chloride particles are mixed with 1 g of the polymer particles described in example 1a) and then treated with 100 ml of a chloroform solution which contains 4 g of the polymer in dissolved form. The mixture which is obtained in this way is heated at from 45° C. to 65° C., resulting in the chloroform evaporating within about 25 minutes. The remaining salt/polymer mixture is then pressed with a hydraulic press for one minute at a ram pressure of 1000 psi and subsequently soaked for 24 hours in order to dissolve out the enclosed salt grains. The matrix is then gassed, as described above, and finally dried for 12 hours on absorbent paper.

The resulting polymer matrix has a porosity of 96%.

If 98.5 g of salt particles are mixed with 0.5 g of polymer particles and the mixture is treated with 100 ml of a chloroform solution which contains 1 g of polymer, a matrix having a porosity of 99% is obtained.

If 99.2 g of salt particles are mixed with 0.1 g of polymer particles and this mixture is treated with 100 ml of a chloroform solution which contains about 0.9 g of polymer, a polymer matrix having a porosity of 99% is obtained.

EXAMPLE 2 a) Coating the Matrix with Fibronectin

The matrix from example 1 is immersed in a carbonate buffer solution which contains 3 µg of human plasma-derived fibronectin (Sigma)/ml and which has a pH of 9.4. After about 60 s, the matrix is taken out of the solution, lyophilized and γ-sterilized.

EXAMPLE 3

Cell Isolation

A portion of liver is removed, in a manner known per se, from the individual to be transplanted. The liver portion which has been removed is first of all perfused for 7 minutes, at a flow rate of 30 ml/min and at 37° C., with a solution (8.3 g of NaCl; 0.5 g of KCl; 2.38 g of HEPES; made up to 1000 ml with distilled water; pH 7.4). The liver portion is then perfused for a further 6 to 7 min, at a flow rate of 30 ml/min and at 37° C., with a collagenase/trypsin inhibitor solution (8.3 g of NaCl; 0.5 g of KCl; 2.38 g of HEPES; 0.7 g of $CaCl_2 \times 2H_2O$; 500 mg of collagenase (collagenase H, Boehringer Mannheim, Mannheim, Germany); 7.5 mg of trypsin inhibitor (ICN, Eschwege, Germany); made up to 1000 ml with distilled water; pH 7.35). After the perfusion has come to an end, the liver portion is dissected out and shaken carefully in Williams medium E. The cell suspension is filtered (nylon net; 200 μm) and then washed with Williams medium E. After that, the cells are centrifuged at 50 g at 4° C. for 3 min. The vitality of the cells, which is determined using Tryptan Blue, is 95%.

Islet of Langerhans cells are isolated from a portion of pancreas in the same way.

EXAMPLE 4

Cell Colonization

In the first step, the matrices which were coated in example 2 are incubated with islet of Langerhans cells which were isolated as described in example 3.

For this, 3000 islet cells were suspended, per ml, in a solution mixture composed of M199 and FCS (volume ratio of 19:1). The cell number is determined by counting it in a 0.25 mm counting tube under an inverted Olympus microscope. From 8 ml to 10 ml of this solution are then applied to the matrix using a pipette. The excess solution which does not remain in the matrix is discarded. The matrix which has been treated in this way is then placed, for 4 hours, in a cell culture incubator in order to allow the cells to adhere. A solution consisting of Williams medium E which, per ml, contains an unpurified liver cell suspension containing about $5.0 \times 10^7$ vital hepatocytes and about $1.0 \times 10^6$ non-parenchymatous liver cells, is then applied to the matrix. From 8 ml to 12 ml of solution are loaded on using a pipette; the excess solution which is not taken up by the matrix is discarded. The matrix can be kept for about 1.5 hours on ice prior to implantation. If an implantation is planned for a later time, the matrix can be stored under standard conditions in a bioflow reactor for up to 5 days.

EXAMPLE 5

Secretory Activity and Rate of Proliferation of the Hepatocytes

Lewis rats were transplanted with cell-colonized matrices as described in example 4. The transplants were removed once again from the animals at various times and examined morphometrically. The number of cells in the transplants, which exhibited the form of a circular disc having a diameter of 15 mm and a thickness of 2 mm, was $94 \times 10^3$, $140 \times 10^3$ and, respectively, $146 \times 10^3$ at 1, 6 and 12 months after transplantation. Hepatocytes from the transplant which is removed one month after transplantation exhibit normal expression of albumin. Proliferating hepatocytes are found in all the preparations without there being any pathological increase in proliferation rate. The hepatocytes which have been transplanted in accordance with the invention exhibit an incorporation of BrdU which is increased by a factor of 3 as compared with that of standard liver preparations.

EXAMPLE 6

Vascularization

Further investigation of the matrices described in example 4 shows that these matrices are outstandingly well vascularized only one month after implantation. The blood vessels extend macroscopically to the matrix and the transplanted hepatocytes and islet of Langerhans cells attain contact as a result of adequate capillarization, with the cardiovascular system of the transplant recipient.

It can furthermore be observed that the cotransplanted islet of Langerhans cells do not cause any hypoglycemia in the recipient. The endocrine secretion performance of these cells, and also of the recipient's own islet cells, is presumably regulated by a feedback mechanism.

EXAMPLE 7

Adoption of Liver Function

Gunn rats are regarded as being an animal model for the human Crigler-Najar syndrome since, as a result of a specific congenital metabolic enzyme defect, their livers are unable to conjugate bilirubin adequately. As a consequence, toxic blood plasma levels of unconjugated bilirubin lead to death as the result of substantial consequential damage.

Three Gunn rats are transplanted with a cell-colonized matrix as described in example 4. The matrix has an external area of in all 10 $cm^2$.

The bilirubin level in the experimental animals falls only four weeks after transplantation. Bilirubin is from now on being conjugated. In all three cases, the conjugated bilirubin can be detected, using a bile duct probe, in the bile ducts of the liver which is still present. Consequently, the bilirubin which is conjugated in the matrix reaches the liver hematogenically and can be eliminated from the liver by way of the bile duct system.

EXAMPLE 8

Human Patients

Cell-colonized matrices as described in example 4 are transplanted into the abdominal cavity of a patient suffering from a pronounced liver cirrhosis. Table 1 below summarizes the patient's laboratory findings prior to the transplantation.

TABLE 1

| Parameter | Patient 1 |
|---|---|
| GOT | 27 |
| GPT | 35 |
| gGt | 89 |
| CHE | 2421 |
| serum albumin | 24.1 |

Patient 1 (ethyl-toxic liver cirrhosis, previously decompensated several times, now not active) was given 4 matrices (in each case 124 mm×45 mm×5 mm).

Table 2 below summarizes the liver values 3, 10 and, respectively, 20 weeks after transplantation.

TABLE 2

| | Patient 1 | | |
| --- | --- | --- | --- |
| | 3 | 10 | 20 |
| GOT | 22 | 10 | 11 |
| GPT | 28 | 9 | 28 |
| gGt | 71 | 10 | 9 |
| serum albumin | 28.6 | 42 | 44 |
| CHE | 2652 | 4400 | 4600 |

The invention claimed is:

1. A method of treating a subject in need of liver or pancreas transplantation, which method comprises obtaining liver and pancreas cells from the subject, inoculating a porous matrix comprising a biologically tolerated polymer with the cells to form an autologous implant, and inserting the autologous implant into the body of the subject, wherein the matrix is inoculated with cells of at least two cell types, wherein the cells of the first cell type are hepatocytes and the cells of the second cell type are islet of Langerhans cells, and wherein the ratio of hepatocytes to islet of Langerhans cells is $10^6$:3-200.

2. The method of claim 1, wherein the subject is in need of liver transplantation and is a subject having chronic hepatitis, billiary cirrhosis, liver carcinoma or liver cirrhosis.

3. The method of claim 1, wherein the subject is in need of pancreas transplantation and is a subject having diabetes mellitus.

4. The method of claim 1, wherein the porous matrix comprises pores having a size of 130 μm or less and pores having a size of 370 μm or more and the degree of porosity is from 93 to 98%.

5. The method as claimed in claim 1, wherein the porous matrix comprises 0.5% to 6% pores having a mean diameter in the range of from 70 to 100 μm; 2% to 8% pores having a mean diameter in the range of from 101 to 115 μm; 2% to 8% pores having a mean diameter in the range of from 116 to 130 μm; 1% to 7% pores having a mean diameter in the range of from 131 to 300 μm; 11% to 23% pores having a mean diameter in the range of from 301 to 330 μm; 4% to 10% pores having a mean diameter in the range of from 331 to 360 μm; 5% to 17% pores having a mean diameter in the range of from 361 to 390 μm; 7% to 19% pores having a mean diameter in the range of from 391 to 420 μm; 3% to 9% pores having a mean diameter in the range of from 421 to 450 μm; 12% to 24% pores having a mean diameter in the range of from 451 to 480 μm; and 5% to 17% pores having a mean diameter in the range of from 481 to 510 μm.

6. The method as claimed in claim 1, wherein the porous matrix comprises 1% to 5% pores having a mean diameter in the range of from 70 to 100 μm; 3% to 7% pores having a mean diameter in the range of from 101 to 115 μm; 3% to 7% pores having a mean diameter in the range of from 116 to 130 μm; 2% to 6% pores having a mean diameter in the range of from 131 to 300 μm; 13% to 21% pores having a mean diameter in the range of from 301 to 330 μm; 5% to 9% pores having a mean diameter in the range of from 331 to 360 μm; 7% to 15% pores having a mean diameter in the range of from 361 to 390 μm; 9% to 17% pores having a mean diameter in the range of from 391 to 420 μm; 4% to 8% pores having a mean diameter in the range of from 421 to 450 μm; 14% to 22% pores having a mean diameter in the range of from 451 to 480 μm; and 7% to 15% pores having a mean diameter in the range of from 481 to 510 μm.

7. The method as claimed in claim 1, wherein the porous matrix comprises 2% to 4% pores having a mean diameter in the range of from 70 to 100 μm; 4% to 6% pores having a mean diameter in the range of from 101 to 115 μm; 4% to 6% pores having a mean diameter in the range of from 116 to 130 μm; 3% to 5% pores having a mean diameter in the range of from 131 to 300 μm; 15% to 19% pores having a mean diameter in the range of from 301 to 330 μm; 6% to 8% pores having a mean diameter in the range of from 331 to 360 μm; 9% to 13% pores having a mean diameter in the range of from 361 to 390 μm; 11% to 15% pores having a mean diameter in the range of from 391 to 420 μm; 5% to 7% pores having a mean diameter in the range of from 421 to 450 μm; 16% to 20% pores having a mean diameter in the range of from 451 to 480 μm; and 9% to 13% pores having a mean diameter in the range of from 481 to 510 μm.

8. The method as claimed in claim 1, wherein the porous matrix comprises 3% pores having a mean diameter in the range of from 70 to 100 μm; 5% pores having a mean diameter in the range of 101 to 115 μm; 5% pores having a mean diameter in the range of from 116 to 130 μm; 4% pores having a mean diameter in the range of from 131 to 300 μm; 17% pores having a mean diameter in the range of from 301 to 330 μm; 7% pores having a mean diameter in the range of from 331 to 360 μm; 11% pores having a mean diameter in the range of from 361 to 390 μm; 13% pores having a mean diameter in the range of from 391 to 420 μm; 6% pores having a mean diameter in the range of from 421 to 450 μm; 18% pores having a mean diameter in the range of from 451 to 480 μm; and 11% pores having a mean diameter in the range of from 481 to 510 μm.

9. The method as claimed in claim 1, wherein the biologically tolerated polymer is albumin, fibrinogen, collagen, gelatin, chitin, chitosan, agarose, alginate, polyanhydrides, poly(ε-caprolactone) or poly(α-hydroxyesters).

10. The method as claimed in claim 1, wherein the biologically tolerated polymer is poly(glycolic acid-lactic acid) having a lactic acid content of 85 mol % and a glycolic acid content of 15 mol %.

11. The method as claimed in claim 1, wherein the surface of the matrix is coated with a coating comprising at least one extracellular matrix protein selected from the group consisting of collagen, laminin and fibronectin.

12. The method as claimed in claim 11, wherein the coating comprises a mixture of type I collagen, laminin and type IV collagen.

13. The method as claimed in claim 1, wherein the matrix is obtained by compacting particles of the polymer and sodium chloride particles and then dissolving out the sodium chloride.

14. The method as claimed in claim 1, wherein the matrix is obtained by adding a polymer solution to a mixture comprising polymer particles and sodium chloride particles and removing the solvent, followed by compacting the remaining mass and then dissolving out the sodium chloride.

15. The method as claimed in claim 14, wherein the solvent dissolves the polymer particles but not the sodium chloride particles.

16. The method as claimed in claim 15, wherein the solvent is acetone, ethyl acetate, methylene chloride, chloroform, hexafluoroisopropanol, chlorinated and fluorinated, aliphatic and aromatic hydrocarbons, tetrahydrofuran, ethyl methyl ketone, diethyl ketone, or a mixture thereof.

17. The method as claimed in claim 14, wherein the polymer solution comprises poly(glycolic acid), poly(lactic acid) or poly(glycolic acid-lactic acid) and chloroform.

18. The method as claimed in claim 14, wherein the ratio by weight of polymer particles to polymer in said polymer solution is from 1:1 to 1:10.

* * * * *